United States Patent [19]
Plotkin et al.

[11] Patent Number: 5,334,772
[45] Date of Patent: Aug. 2, 1994

[54] POLYALK-1-ENYL ETHERS

[75] Inventors: Jeffrey S. Plotkin, Monsey, N.Y.; Kolazi S. Narayanan, Palisades Park; Paul D. Taylor, West Milford, both of N.J.

[73] Assignee: ISP Investments Inc., Wilmington, Del.

[21] Appl. No.: 867,563

[22] Filed: Apr. 13, 1992

Related U.S. Application Data

[63] Continuation-in-part of Ser. No. 417,135, Oct. 4, 1989, abandoned.

[51] Int. Cl.$^5$ .............................. C07C 43/11
[52] U.S. Cl. ........................... 568/609; 568/616; 568/608
[58] Field of Search ............... 568/608, 609, 616

[56] References Cited

U.S. PATENT DOCUMENTS 4,954,582  9/1990  Liu ..................................... 568/609

FOREIGN PATENT DOCUMENTS 2095686  10/1982  United Kingdom .

*Primary Examiner*—Paul J. Killos
*Attorney, Agent, or Firm*—Marilyn J. Maue; Joshua J. Ward

[57] ABSTRACT

This invention relates to the polyalk-1-enyl ethers having the formula

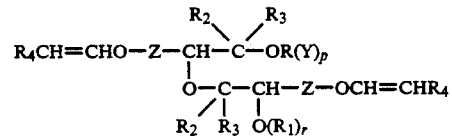

which is the reaction product of a hydroxylated compound and an alk-1-enyloxy oxirane and to the process for preparing the polyalk-1-enyl ether product.

10 Claims, No Drawings

POLYALK-1-ENYL ETHERS

CROSS-REFERENCE TO RELATED PATENT APPLICATIONS

This application is a continuation-in-part of Ser. No. 417,135, filed on Oct. 4, 1989, abandoned.

In one aspect this invention relates to novel polyalk-1-enyl ethers which can be cationically cured by heat or light radiation to form coatings and adhesives. In another aspect the invention relates to the reaction composition and the process for preparing said polyalk-1-enyl ethers.

BACKGROUND OF THE INVENTION

Polyallyl ethers derived from polyols and carbohydrates, particularly allylated pentaerythritol, trimethylpropane, starches and sugars have been widely investigated as monomers suitable for protective coatings. These materials are attractive since they undergo autoxidative polymerization in contact with air. However, because of slow curing rates, color formation and relatively poor substrate bonding strength, films of these allyl ethers have limited commercial use (see ALLYL COMPOUNDS AND THEIR POLYMERS by C. E. Schildknecht, Wiley Interscience, 1973). Additionally many of these monomers and oligomers are thermally unstable and decompose to give off an objectionable odor characteristic of acrolein.

Attempts to prepare high molecular weight monoallyl ethers by free radical or ionic polymerizations have not been successful and result in low molecular weight products in admixture with substantial quantitites of unreacted material which is difficult to separate. According to British Patent 730,670, the polymerization of a allyl glycidyl ether benzene solution in the presence of 3% ditertiary butyl peroxide at 155° C. resulted in a product having a molecular weight of only 500 which was contaminated with a significant quantity of unconverted allyl glycidyl ether. Obviously such materials are unsuitable as protective coatings.

Although esters, which are electron accepting and require free radical initiation for UV curing, are not comparable to electron donating ethers which are highly reactive in cationically induced reactions, it is noted for the sake of full disclosure that certain ester blends of acrylated bisphenol A epoxy resins and ester blends of acrylated aromatic urethanes have been cured by UV exposure to provide rigid coatings. This work is reported by Byron K. Christmas et al. in 1988 (Specialty Chemicals 8(1) 24-6). However, these ester blends are not UV curable by cationically induced systems. Thus, as to be expected, their curing rates are comparatively slow, i.e. 7.5-100 ft/min with few exceptions up to 150 ft/min as compared to 300-500 ft/min achieved with cationically initiated UV radiation. Also, the coating properties of these blends display highly unpredictable results ranging from 0%-100% adhesion and MEK resistance from 1 to about 50 in most cases.

Accordingly, it is an object of the present invention to avoid the use of esters and to overcome the above deficiencies by the use of certain alkenyl derived ethers which are readily polymerizable in cationically initiated systems to provide thermally stable compounds having superior coating properties.

Another object is to provide films which consistently show good adhesion and high resistance to chemical attack.

Another object of this invention is to provide an economical and commercially feasible process for rapid curing of coatings.

Still another object is to provide metal and glass coatings and finishes which are not subject to coloration over extended periods of use.

These and many other objects of the invention will become apparent from the following description and disclosure.

THE INVENTION

In accordance with this invention there is provided a novel, cationically induced radiation curable polyalk-1-enyl ether monomer, oligomer or polymer which is prepared by the reaction of an alk-1-enyloxy oxirane with a mono- or poly- hydroxylated compound wherein an excess of at least 2:1 epoxide to hydroxy group is employed. The reaction is defined by the following equation:

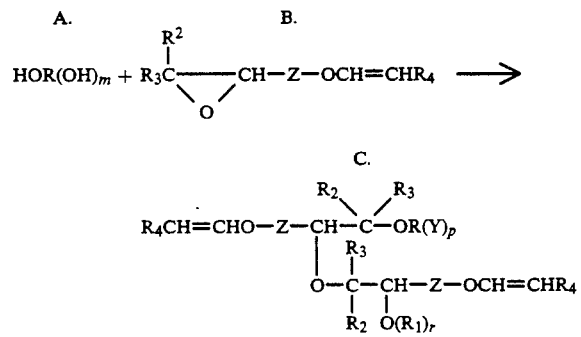

wherein m and p have a value of from 0 to 8; when p has a positive value, R is a divalent $C_2$ to $C_{20}$ aromatic or aliphatic hydrocarbon, radical optionally substituted with halo, carbonyl, vinyl ether, carboxylate, carbonate, hydroxy, alkoxy, alkyleneoxyalkyl and alkenyleneoxyalkyl; when p is zero, R is a monovalent $C_2$ to $C_{20}$ optionally alkoxylated radical of alkyl, phenyl, benzyl, a polyhydroxylated starch, sugar, cellulose or the radical:

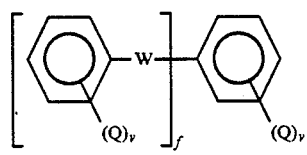

where

W is $C_1$ to $C_4$ alkyl, sulfur, sulfonyl or oxygen, f has a value of from 1 to 50, Q is halo or $C_1$ to $C_4$ alkyl and v has a value of 0–4;

$R_2$ and $R_3$ are each independently hydrogen, $C_1$ to $C_6$ alkyl, alkenyl, haloalkyl or haloalkenyl;

$R_4$ is hydrogen or $C_1$ to $C_6$ alkyl;

Z is an optionally alkoxylated $C_1$ to $C_8$ aliphatic hydrocarbon;

Y is hydrogen, hydroxy or

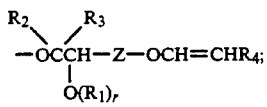

r has a value of from 1 to 100, depending on the stoichiometric ratio of reactant B to reactant A and $R_1$ is hydrogen when r is 1 and, when r is positive, $R_1$ is

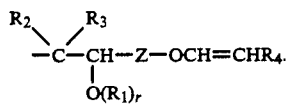

* The term "divalent aliphatic hydrocarbon" as used herein denotes an alkylene, alkenylene, alkynylene, aaralkylene or aralkenylene radical or a polymer of the type $$-[-C_6H_4-\text{alkylene}-]_tC_6H_4-,$$

composed of carbon and hydrogen. The term "divalent aromatic hydrocarbon" denotes an optically alkyl or alkenyl substituted arylene radical, also composed of carbon and hydrogen.

Thus, increasing amounts of epoxide component in the reaction mixture are reflected in a corresponding progression of ring opened oxide groups substituted in the molecule of the final product.

In the above condensation reaction an excess of reactant B is generally employed. Preferably the mole ratio of component A to B varies from about 1:1.5 to 1:300. For example when reactant B is the alk-1-enyloxy oxirane

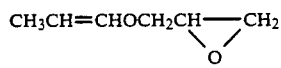

employed in a mole ratio of 8:1 with respect to reactant A which is bisphenol A, $HO-C_6H_4-C(CH_3)_2-C_6H_4-OH-$, the product of the reaction is usually in admixture with isomeric forms thereof, e.g. where the sum of $R_1$ substituents in the compound is equal to 8. Thus, some species may not be symmetrical and may have, for example two ring opened radicals substituted on the oxygen of one phenyl and six ring opened radicals substituted on the oxygen of the other phenyl radical or one ring opened radical on the oxygen of one phenyl and 7 ring opened radical substituted on the oxygen of the other phenyl radical.

When the same condensation reaction is carried out using a 4:1 molar ratio of B to A, the corresponding product has the structure

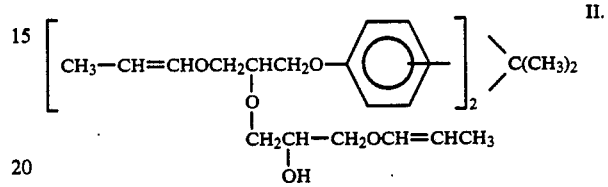

II.

usually in admixture with isomeric forms thereof as explained above.

It is to be understood that the products of this invention, in addition to their individual isomeric forms, can also be in the form of a cis and trans isomeric mixture wherein the ratio of cis to trans is dependent on the isomeric ratio in the alk-1-enyl oxirane reactant. More often the products of this invention are mixtures of cis and trans isomers.

It will be understood that when other polyols, such as tri- and tetra- hydroxylated reactants are involved, the same condensation reactions shown above can occur at the hydroxy sites of the hydroxylated reactant; thus leading to highly substituted products depending upon the particular polyol and the molar ratio of the respective reactants.

The following formula III illustrates a reaction product of a phenol-formaldehyde condensation resin and (prop-1-enyloxy methyl) oxirane, where the molar ratio of oxirane per —OH group is 4:1.

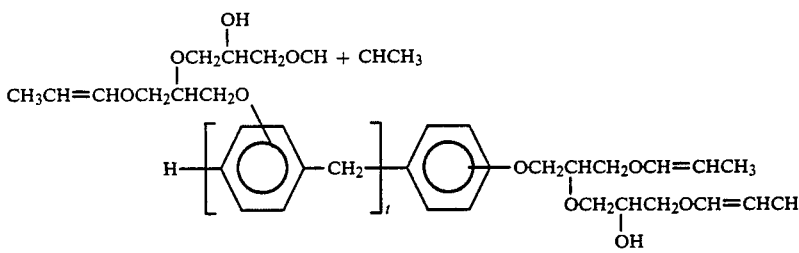

III.

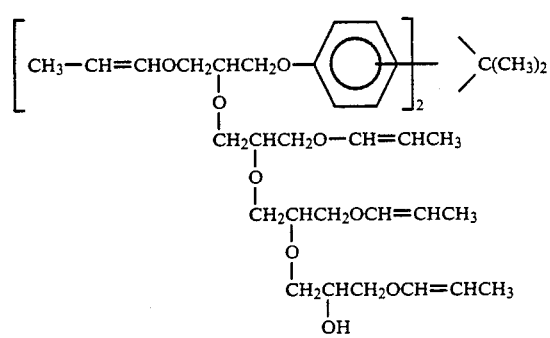

I.

where t has a value of from 10 to 40.

The product obtained from (prop-1-enyloxy methyl) oxirane and pentaerythritol in molar proportion of 8:1 is

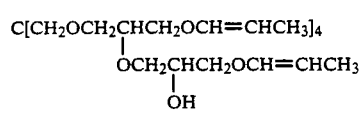

IV.

This product may also contain some mono-, di- and/or tri-substituted species, e.g.

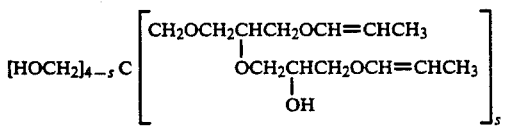

where s has a value of from 1 to 4.

The product obtained from 1,3,4-trihydroxy butane and prop-1-enyloxy methyl oxirane in a ratio of 1:4 can be

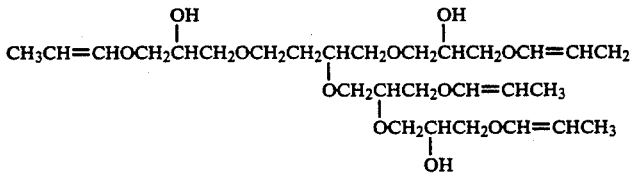

V.

and isomeric mixtures thereof. However, the excess of epoxide is controlled such as to allow at least one

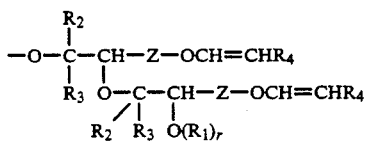

group in the product.

As pointed out above, the hydroxy-containing reactant can have a linear, branched, cyclic aliphatic or aromatic structure and can be monomeric or polymeric. Examples of suitable hydroxylated reactants include polyalkylene glycols, hydrogenated bisphenol A, halogenated bisphenol A, bisphenol A, alkoxylated bisphenol A, dihydroxyphenyl ether, resorcinol, hydroquinone, tetrahydrofuran dimethanol, petunidin chloride, methyl hydroxypentanol, pentaerythritol, trimethylol propane, trimethylol ethane, dihydroxyethylbenzoate, dihydroxy naphthyl hexanone, phenol, bisphenol, polyphenol, methanol, ethanol, propanol, butanol, octanol, 1,4,6-trihydroxyoctane, 2,4,6,8,10-pentahydroxy dodecane, ethylene glycol, propylene glycol, ethylene chlorohydrin, butanediol, phenaglycodol, butenediol, butynediol, glycerol, glyceryl, hydroxybutyl vinyl ether, monochlorohydrin, cresol, benzyl alcohol, hydroxy-methyl acetophenone, cresyl acetate, cyclohexanol, halogenated phenols, catechol, hexylresorcinol, trihydroxybenzene, a phenol-formaldehyde condensate resin, tetrahydroxybenzene, dihydroxy phenyl methane, trihydroxy butane, tetralol, naphthol, anthranol, etc. and natural alcohols such as cellulose, starches, and sugars and alkoxylated derivatives thereof.

The alk-1-enyloxy oxirane reactant contains from 5 to 28 carbon atoms, examples of which include 1-methyl-2-(prop-1-enyloxy) oxirane, (3-ethenyloxy propyl) oxirane, (4-ethenyloxy-butyloxy) methyl oxirane, 1-butyl-2-[2-(but-1-enyloxy) ethyl] oxirane, [4-(prop-1-enyloxy) butyl] oxirane, [2-(prop-1-enyloxy) ethyl] oxirane, 1-butyl-2[(but-1-enyloxy) ethyl] oxirane, [(prop-1-enyloxy) methyl] oxirane, [2-(vinyloxy) ethyl] oxirane, 1-ethyl-2-[(prop-1-enyloxy)methyl] oxirane, 1-methyl-1-ethyl-2-[3-(hex-1-enyloxy)propyl] oxirane, 1-methyl-2-[2-(but-1-enyloxy) ethyl] oxirane, 1-ethyl-2-[4-(vinyloxy)butyl] oxirane, (ethenyloxy methyl) oxirane, 1-propyl-2-[2-(prop-1-enyloxy) ethyl] oxirane, 1,1-dimethyl-2-[2-(but-1-enyloxy) ethyl] oxirane, 1-hexyl-2-[8-(prop-1-enyloxy) octyl] oxirane, etc.

The mole ratio of hydroxylated compound to total oxirane reactant can range up to about 1:300, depending upon the number of —OH groups in the hydroxylated compound, the stoichiometric ratio of oxirane/—OH and the degree of —H substitution desired. More desirably, when the hydroxylated compound is a diol, a mole ratio of between about 1:4 and 1:32 diol to oxirane is employed. When the hydroxylated compound is an polyhydroxy alkane containing up to 4 hydroxy groups, e.g. pentaerythritol, tetrahydroxy butane, etc. the mole ratio of hydroxylated alkane to oxirane is between about 1:8 and 1:28.

The reaction is carried out in the presence of a base catalyst such as, e.g. sodium or potassium metal, sodium or potassium methoxylate, hydroxide, alkoxide, hydride, phenoxide, or an alkaline earth metal hydroxide or alkoxide. Also, alkali or alkaline earth metal salts of reactant A can be employed. The catalyst is employed in a concentration of between about 0.1 and about 5 wt. %, preferably between about 0.4 and about 1 wt. %, based on total reactants.

In cases where the mixture of reactants provides a liquid having a viscosity such that good agitation becomes difficult, up to about 90 wt. % of an inert solvent can be added to the mixture. Suitable solvents include toluene, xylene, benzene; ethers such as alkyl ethers, e.g. methyl ethyl ether, diethyl ether, dibutyl ether, 1,2-dimethoxyethane, bis(2-methoxyethyl) ether, tetrahydrofuran; ketones such as methyl ethyl ketone; amides such as N-methyl-pyrrolidone, dimethyl formamide, N-ethyl-pyrrolidone;esters such as butyrolactone and ethyl acetate; nitriles such as acetonitrile and benzonitrile, cyclic carbonates such as ethylene and propylene carbonates and the like which have a boiling point below that of the reaction product.

The present reaction is effected in the liquid phase by agitating the reactants under a blanket of inert gas, e.g. nitrogen, argon, etc., at a temperature within the range of between about 50° and about 150° C. under from about atmospheric pressure up to about 1,000 psi when volatile reactants are employed in the reaction mixture. The reaction takes place over a period of from about 1 to 48 hours. Preferred reaction conditions include a temperature of between about 90° and about 135° C. under a pressure not exceeding 200 psi for a period of from about 2 to 20 hours.

When the reaction product is highly viscous, any of the above named solvents can be added for dilution and the crude reaction mixture treated to remove catalyst. For example water can be added to the mixture to form a 2-phase liquid and to take up catalyst in the aqueous phase. The organic phase containing product is separated from the aqueous phase and dried to remove water and any solvent which may have been added to lower viscosity is removed under reduced pressure. Alternatively, a weakly acid ion exchange resin, e.g. Amberlite, IRC-50 or an inorganic adsorbent such as Magnesol, can be added to the reaction mixture to precipitate the catalyst whereupon the desired product is recovered by filtration.

The products of this process are useful as molding resins, adhesives and as highly solvent resistant coating materials which undergo substantially instantaneous curing thermally or curing by irradiation in cationic initiated systems to provide clear, colorless, flexible films when applied to a substrate.

Having thus generally described the invention, reference is now had to the accompanying examples which illustrate preferred embodiments but which are not to be construed as limiting to the scope of the invention as more broadly set forth above and in the accompanying examples.

EXAMPLE I

In a 500 ml 3-necked round bottomed glass flask equipped with a mechanical stirrer, a thermometer, a water condenser and a nitrogen inlet was mixed 57 g. of bisphenol A, 230 g. of 74%-26% cis/trans [(prop-1-enyloxy)methyl] oxirane (mole ratio of 1:8). To this mixture, 2.5 g. of NaOCH$_3$ was added and the resulting mixture agitated under a blanket of nitrogen. After 12 hours at 130° C. under ambient pressure proton NMR indicated completion of the reaction and 250 cc of toluene was then added. The reaction product was recovered by washing with three 250 g. portions of H$_2$O, thus forming an aqueous phase and an organic phase. The organic layer containing product was separated, dried with magnesium sulfate, filtered and toluene was evaporated under reduced pressure. A clear yellow liquid, 225 g., of the product having the formula

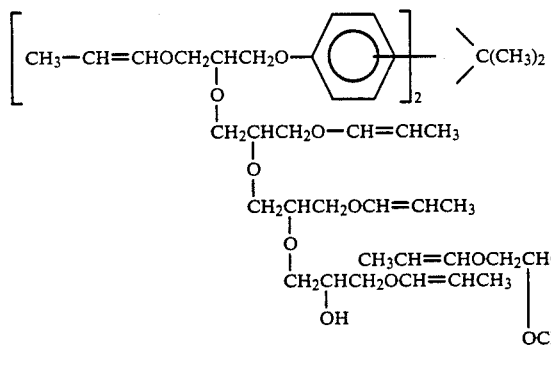

was recovered in admixture with isomeric species thereof.

The above reaction was repeated except that 54%-46% cis/trans [(prop-1-enyloxy)methyl] oxirane was substituted. The substitution of this reactant had no material affect and the product was identical to that described above except for the cis/trans product distribution.

EXAMPLE II

Example I is repeated except that 114 g. of the oxirane reactant (54%-46% cis/trans) was employed to provide a mole ratio of 1:4. The resulting product

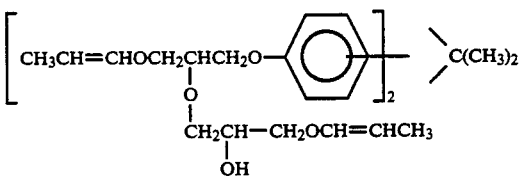

was obtained in 94% yield.

EXAMPLE III

Example I is repeated except that 114 g. of the oxirane reactant was employed to provide a 1:4 mole ratio and resorcinol is substituted for bisphenol A. The product having the formula

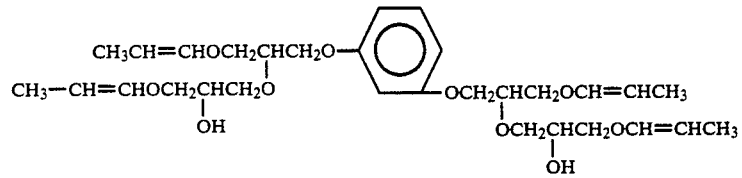

is recovered in 95% yield.

EXAMPLE IV

In a reactor similar to the one described in Example IV. Bisphenol A (114 g.), 250 g. of [(prop-1-enyloxy)-methyl] oxirane (74%-26% cis/trans) i.e. a mole ratio of 1:4 and 5 g. of sodium methoxide were stirred at 130° C. under a blanket of nitrogen. After 5 hours the reaction was complete as indicated by proton NMR spectroscopy. The product, 320 g., of a yellow oily liquid having the formula

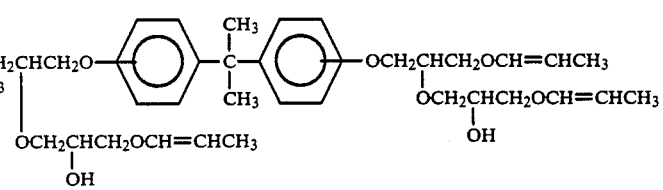

as indicated by proton NMR spectrum was recovered in admixture with a minor amount of isomers thereof.

Other examples employing different els/trans ratios, e.g. 54%-46%, were employed but found to have no material effect on the reaction or product obtained.

EXAMPLE V

To a glass reactor equipped with a mechanical stirrer, thermometer, condenser, and nitrogen inlet 114 g. of [(prop-1-enyloxy)methyl] oxirane, 57 g. of hydrogenated bisphenol A and 0.5 g. of sodium methoxide were charged. This mixture was stirred and maintained at 130° C. for 16 hours. To remove the base catalyst the crude product was diluted with 150 cc of tetrahydrofuran and slurried vigorously with 5 g. of Magnesol for one hour. The Magnesol was then filtered off and the tetrahydrofuran removed under reduced pressure. The remaining product was a yellow viscous liquid which slowly solidified upon standing after several days. This product had the structure

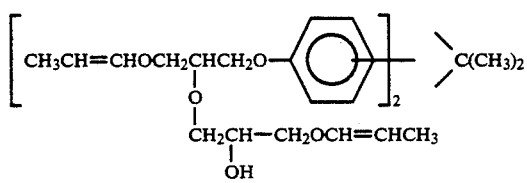

which was obtained with isomers thereof.

EXAMPLE VI

To a glass reactor equipped with a thermometer, mechanical stirrer, condenser and nitrogen inlet 230 g. of [(prop-1-enyloxy)methyl] oxirane, 34 g. of pentaerythritol, and 0.5 g. sodium methoxide are charged. This mixture was stirred and heated to 115° C. under nitrogen for 5 hours. The catalyst is removed as in Example VII by treatment with Magnesol, after which a clear yellow liquid product having the formula

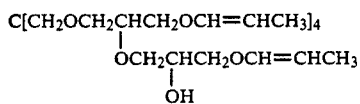

is obtained in mixture with less than 5% of the corresponding mono-, di- and tri- substituted products.

EXAMPLE VII

Example II is repeated except that 344 g. of [4-(ethenyloxy) butyloxy methyl ] oxirane is substituted for [(prop-1-enyloxy)methyl] oxirane. Using the 1:4 molar ratio, the resulting product

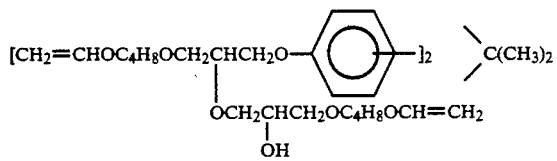

in isomeric mixture is obtained in 90% yield.

EXAMPLE VIII

Example II is repeated except that [(ethenyloxy)methyl] oxirane is substituted for [(prop-1-enyloxy)methyl] oxirane and diphenol is substituted for bisphenol A. Using a 1:4 molar ratio, the resulting product,

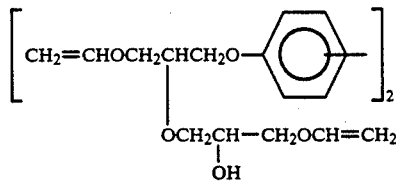

in isomeric mixture is recovered in 95% yield.

EXAMPLE IX

In a 1 liter glass reactor equipped with a mechanical stirrer, thermometer, condenser, and nitrogen inlet is added 127 g. of phenol, 685 g. of [(prop-1-enyloxy)methyl] oxirane and 25 g. of sodium methoxide. This mixture is stirred at room temperature under a blanket of nitrogen for 7 hours. Due to exothermic conditions the temperature is increased to 150° C. After 3 hours the reaction is cooled to about room temperature whereupon the product is recovered in 90% yield by flash distillation under reduced pressure. The resulting product has the structure:

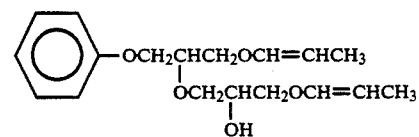

EXAMPLE X

Example VIII is repeated except that 1,3,6,8-tetrahydroxy decane is substituted for diphenol and an 8 molar excess of (eth-1-enyloxy) methyl oxirane is added. The product having the formula

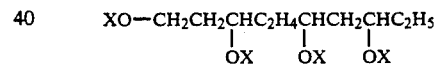

in isomeric mixture where X is

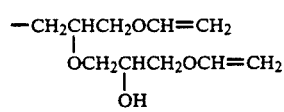

is recovered.

EXAMPLE XI

A 500 ml 3-necked round bottomed flask equipped with a mechanical stirrer, thermometer, water condenser and nitrogen inlet is charged with 114 g. of m,m'-dichloro bisphenol A, 250 g. of [(prop-1-enyloxy)-methyl] oxirane (74%-26% cis/trans), i.e. a mole ratio of 1:4, and 2.5 g. of sodium methoxide. The flask is heated to 130° C. and stirred for 5 hours under nitrogen. Progress of the reaction is monitored by withdrawing samples of the reaction mixture every hour via proton NMR. The product mixture is then diluted with 250 ml of toluene.

The product is recovered by washing with three 250 g. portions of water. The resulting organic layer is separated from the aqueous layer and dried with magnesium sulfate, filtered, and the toluene removed under reduced pressure. The final product (about 400 g.) is a clear yellow viscous liquid having the formula

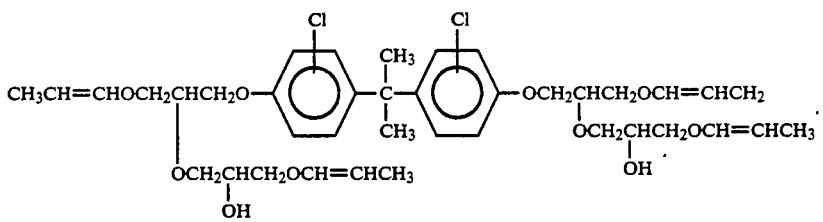

It will be understood that many modifications and substitutions can be made in the above examples to provide the novel compounds of this invention. For example, other oxiranes, such as [(but-1-enyloxy)butyl] oxirane, [(pent-1-enyloxy)butenyl] oxirane, [(prop-1-enyloxy)methyl] dimethyl oxirane, butenyloxy ethyl epoxide and the like can be substituted in any of the foregoing examples. Also, other hydroxylated compounds can be substituted therein. For example monohydroxylated and polyhydroxylated alkanes of 2 or more carbon atoms, a starch or a sugar, an polyethoxylated or polypropoxylated butanediol, dichlorobutanediol, and the like are representative. All of the above are included in the scope of this invention.

What is claimed is:

1. The polyalk-1-enyl ether having the formula

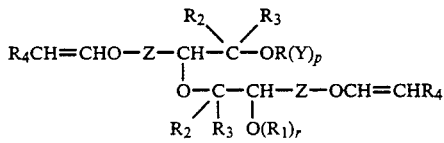

wherein p has a value of from 0 to 8; when p has a positive value, R is the radical:

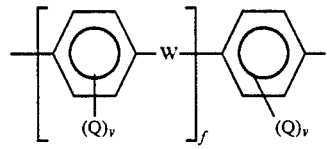

where W is $C_1$ to $C_4$ alkyl, sulfur, sulfonyl or oxygen, f has a value of from 1 to 50, Q is halo or $C_1$ to $C_4$ alkyl and v has a value of 0–4; when p is zero, R is a monovalent $C_2$ to $C_{20}$ optionally alkoxylated radical of alkyl, phenyl, benzyl, or the radical:

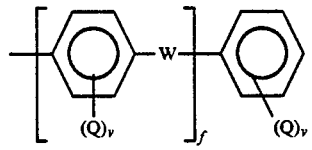

where
W is $C_1$ to $C_4$ alkyl, sulfur, sulfonyl or oxygen, f has a value of from 1 to 50, Q is halo or $C_1$ to $C_4$ alkyl and v has a value of 0–4;
$R_2$ and $R_3$ are each independently hydrogen or $C_1$ to $C_6$ alkyl;
$R_4$ is hydrogen or $C_1$ to $C_6$ alkyl;
Z is an optionally alkoxylated $C_1$ to $C_8$ aliphatic hydrocarbon;
Y is

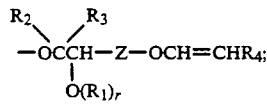

r has a value from 1 to 100, and $R_1$ is hydrogen when r is 1 and, when r is greater than 1, $R_1$ is

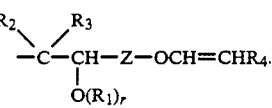

2. The polyalk-1-enyl ether of claim 1 wherein p has a positive value.

3. The polyalk-1-enyl ether of claim 2 wherein R is

4. The polyalk-1-enyl ether of claim 3 wherein R is —$C_6H_4$—$C(CH_3)_2$—$C_6H_4$—.

5. The polyalk-1-enyl ether of claim 4 having the formula

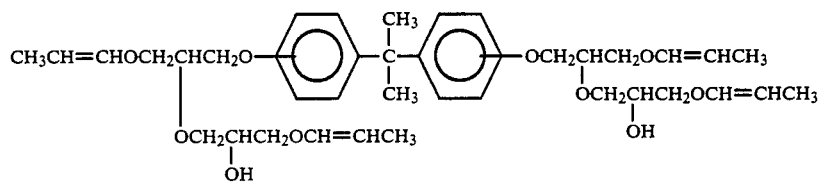

6. The polyalk-1-enyl ether of claim 4 having the formula

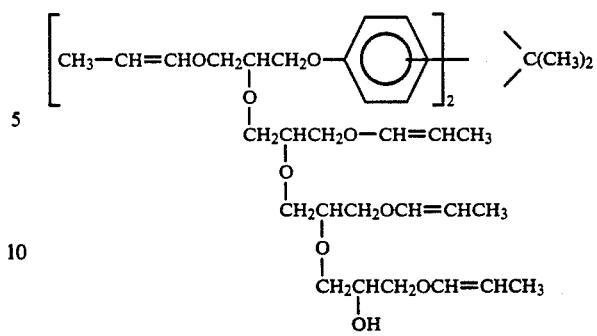
7. The polyalk-1-enyl ether of claim 4 having the formula
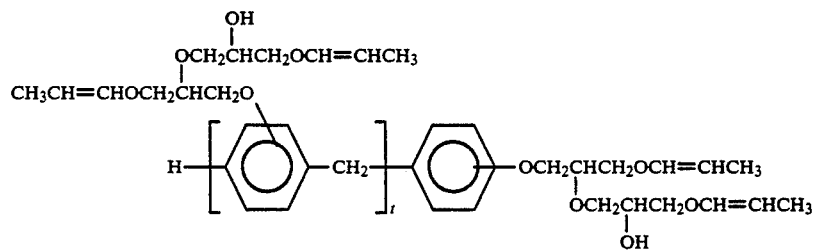
8. The polyalk-1-enyl ether of claim 1 wherein $R_4$ is hydrogen or methyl.
9. The polyalk-1-enyl ether of claim 1 wherein $R_2$ and $R_3$ are hydrogen.
10. A cationically curable, abrasion resistant coating of the polyalk-1-enyl ether of claim 1 on a substrate.
* * * * *